United States Patent [19]

Delsanti

[11] Patent Number: 4,998,539
[45] Date of Patent: Mar. 12, 1991

[54] METHOD OF USING REMOVABLE ENDO-ARTERIAL DEVICES TO REPAIR DETACHMENTS IN THE ARTERIAL WALLS

[76] Inventor: Gerard L. Delsanti, 15 Les Helianthes, 13390 Auriol, France

[21] Appl. No.: 283,729

[22] Filed: Dec. 13, 1988

[30] Foreign Application Priority Data

Dec. 18, 1987 [FR] France .................. 87 17975

[51] Int. Cl.$^5$ ............................................. A61M 29/00
[52] U.S. Cl. .................... 128/898; 606/198; 606/194
[58] Field of Search ............ 128/343, 345, 341, 348.1, 128/898; 604/104, 107; 606/108, 153, 155, 156, 198, 200, 194

[56] References Cited

U.S. PATENT DOCUMENTS

| | | | |
|---|---|---|---|
| 3,868,956 | 3/1975 | Alfidi et al. | 128/345 |
| 3,996,938 | 12/1976 | Clark | 128/348.1 |
| 4,512,338 | 4/1985 | Balko et al. | |
| 4,572,186 | 2/1986 | Gould et al. | 604/104 X |
| 4,619,246 | 10/1986 | Molgaard-Nielsen et al. | |
| 4,650,466 | 3/1987 | Luther | |
| 4,655,771 | 4/1987 | Wallsten | 128/343 X |
| 4,706,671 | 11/1987 | Weinrib | |
| 4,723,549 | 2/1988 | Wholey et al. | 604/101 X |
| 4,776,337 | 10/1988 | Palmaz | 128/343 |
| 4,848,342 | 7/1989 | Kaltenbach | 606/198 |

Primary Examiner—Michael H. Thaler
Attorney, Agent, or Firm—Fulwider, Patton, Lee & Utecht

[57] ABSTRACT

A removable endo-arterial device intended to repair detachments in arterial walls which includes a deformable cuff made of netting of interlocked wires and fixed to the distal end of a catheter, the other end of which is equipped with a funnel. The device also includes a stiff wire extending over the entire length of the catheter and attached to the distal end of said deformable cuff. When this wire is pulled, the cuff is dilated and applies itself against the arterial wall. Preferably, an inflatable balloon is disposed within the cuff to facilitate the expansion thereof. One application of the invention is the repair of flaps of arterial wal which are detached during the course of an intervention correcting a stenosis with an inflatable balloon.

3 Claims, 2 Drawing Sheets

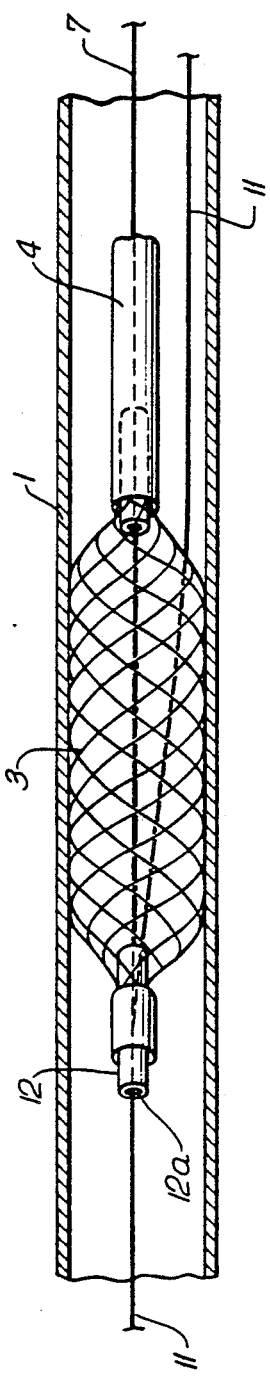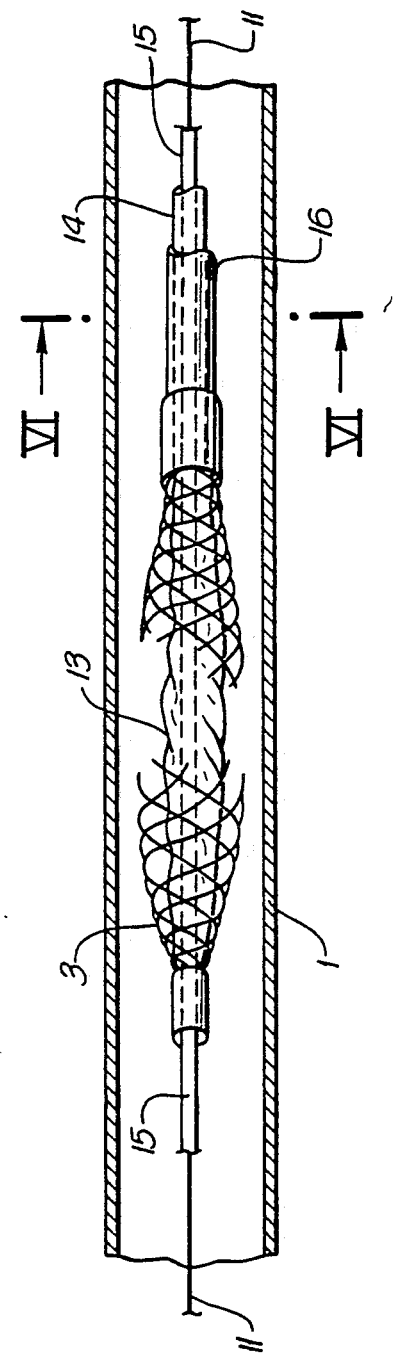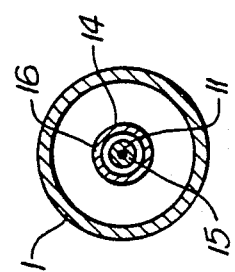

METHOD OF USING REMOVABLE ENDO-ARTERIAL DEVICES TO REPAIR DETACHMENTS IN THE ARTERIAL WALLS

The present invention covers endo-arterial devices temporarily installed in an artery in order to re-attach flaps which have been detached from the wall.

The technical field of the invention is the construction of surgical equipment used in cardio-vascular interventions.

There are known devices consisting of a small inflatable balloon at the end of a catheter used to dilate strictures in the arteries, especially the coronary arteries.

Such a catheter bearing a balloon is introduced into an artery, for example into the femoral artery, until the balloon reaches the stricture. The ballooon is then inflated with a fluid pumped in through the catheter and pushes back the arterial wall thus eliminating the stricture. The balloon must then be deflated very quickly, since it blocks the artery and impairs the blood circulation.

It so happens that a similar intervention may cause detachments of the part of the arterial wall called intima, and the detached wall flaps inhibit the blood circulation and may result in severe and even fatal accidents if the circulation is interrupted.

Devices consisting of a cylindrical elastic cuff inserted over an inflatable balloon fixed to the end of a catheter have been tried for the prevention of such accidents.

The balloon is folded back over the cuff so as to keep the latter in an elongated shape of small diameter while it is being pushed through the arteries.

Once the balloon bearing the elastic cuff has arrived at the site of the wall detachment, it is inflated so that the folded part slips loose releasing the cuff which increases in diameter and plasters itself against the internal wall of the artery where it remains indefinitely.

This device prevents the inconvenience of introducing a foreign body into the artery to remains stationary there with all the risks of blood clots which this implies.

The object of the present invention is attained with a device consisting of a deformable cuff made up of a net of twisted and interlocking wires mounted at the end of a catheter which is then introduced into an artery. It also includes some means activated from the external end of said catheter to move the two ends of said deformable cuff closer together or farther apart in order to give said cuff a wider shape which presses it against the arterial wall or a flat, elongated shape which permits introduction of the cuff and catheter into the artery or their withdrawal.

According to the preferential embodiment of said invention, the means used to reduce or extend the distance between the two end of the deformable cuff are made up by a wire of the piano wire type which makes it possible to exert a push and which is fixed to the distal end of said cuff while freely passing through the proximal end of it and extending through the entire length of said catheter.

According to another embodiment, a device under this invention includes, in addition, an inflatable balloon located inside said deformable cuff and is mounted at the end of an inflation tube which, in turn, runs inside said catheter.

The invention produces new devices usable in cardiovascular interventions, especially in interventions intended to remove stenoses of the coronary arteries in case of a severe risk of infact or after an infarct has occurred.

The devices according to this invention present the advantage that the deformable net allows the blood to pass between the mesh openings when it is applied against the wall of an artery. It can therefore be left in place for a duration on the order of one or more hours which is more than sufficient to ensure cicatrization of the flaps detached from the arterial wall.

As compared to the known devices which involve an elastic cuff remaining stationary in the artery, the devices under this invention have the advantage of being removable so that there is no risk of rejection phenomena or of the formation of blood clots. The devices under this invention include an inflatable balloon placed inside a cuff or deformable net which makes it possible to treat a stenosis and, if necessary, to immediately repair the arterial wall. They therefor reduce the risk of postoperative complications and can even be used for interventions on strictures of the common trunk of the coronary arteries.

The following description refers to the enclosed drawings which represent examples of embodiments of the devices under this invention without being in any way limitative.

FIG. 4 is a longitudinal section of a second embodiment of a device according to this invention.

FIG. 5 is a longitudinal section of a third embodiment of a device according to this invention.

FIG. 6 is a cross secton along VI—VI in FIG. 5.

Figure 1:
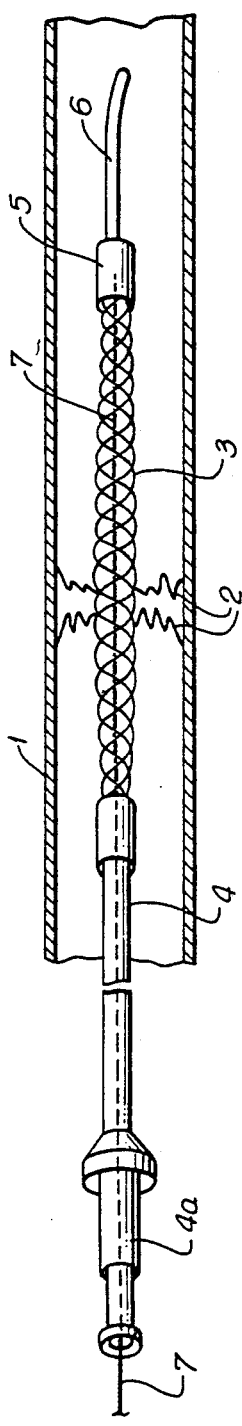
FIG. 1 is a longitudinal section of a first embodiment of a device according to this invention, in an elongated position.

FIG. 1 shows a longitudinal section of an artery 1 which could be a coronary artery presenting a stricture or stenosis. During a first intervention, a catheter bearing an inflatable balloon at the end has been inserted into the artery until said balloon reached the stenosis. The balloon was then inflated with a fluid pumped in through the catheter. The inflated balloon has pushed the arterial wall back and removed the stenosis. Since the inflated balloon blocks the artery, it had to be quickly deflated.

The inflating and deflating operation of the balloon may be repeated several times.

Subsequently, the balloon and catheter are withdrawn. It happens that during these operations, the internal wall of the artery, called intima, suffered some detachments 2 which could block the artery and result in the death of the patient.

A device according to this invention is a removable endoarterial prothesis intended to reduce these risks by applying the detached flaps of wall against the artery long enough for cicatrization to take place.

FIG. 1 shows a device according to this invention in its elongated shape which makes it possible to introduce or withdraw it from the artery.

Figure 2:
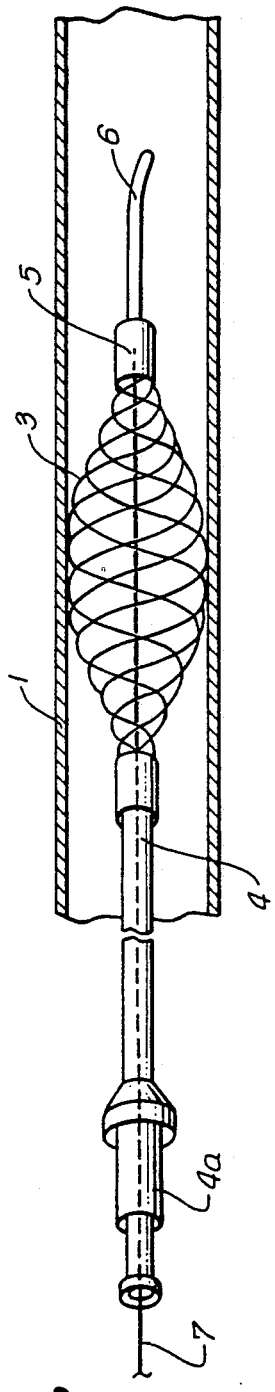
FIG. 2 is a longitudinal section of a device according to FIG. 1 in the deployed position.

FIG. 2 represents a device according to the invention in its deployed form in which it is widened so that it presses the detached wall flaps against the artery.

A device according to the invention includes a deformable cuff 3 made of a net of twisted and interlocked wires which could, for instance, be of stainless steel wires or of any other material having equivalent properties of compatibility with the blood.

The deformable cuff 3 is fixed to the end of a small flexible tube 4 which has a diameter on the order of a few millimeters and serves as catheter.

The distal end of the deformable cuff 3 is fixed to a small muff 5 on which a small flexible axial rod 6 is mounted which procedes the deformable cuff 3 and serves as guide for the latter along the artery.

A device according to FIGS. 1 and 2 includes, in addition, an axial wire 7 of the piano-wire type which is fixed to the distal end of cuff 5, passes through the latter and extends over the entire length of the catheter.

The catheter is equipped at its outer end with a funnel 4a of a known kind, for example a funnel of the "LU-ER-LOCK" type. Wire 7 passes through the connection 4a, so that its end is accessible outside the catheter.

The practical application of a device according to FIGS. 1 and 2 is the following:

The catheter bearing at its end a deformable cuff 3 which is fully elongated as shown in FIG. 1 and which therefore has a very small cross section is introduced into the artery. The progress of cuff 3 is controlled by radiography. When it reaches the area of the former stenosis, the end of wire 7 is pulled while the catheter is held in place in the artery. The pull exerted on said wire has the effect of bringing the distal end of cuff 3 close to its proximal end.

The cuff dilates as shown in FIG. 2 and comes to rest against the arterial wall, thus pressing the detached flaps back against said wall. Cuff 3 is left in this position for as long as one or more hours, since the blood can freely circulate through the mesh openings of the cuff which at that time are open. When it is deemed that sufficient time has elapsed for the flaps to adher again to the wall, the outer end of wire 7 which is stiff enough not to bend is pushed and causes the distal end 5 of cuff 3 to move away, so that the cuff is again in its elongated position. The catheter 4, wire 7 and cuff 3 are them withdrawn together from the artery.

Figure 3:
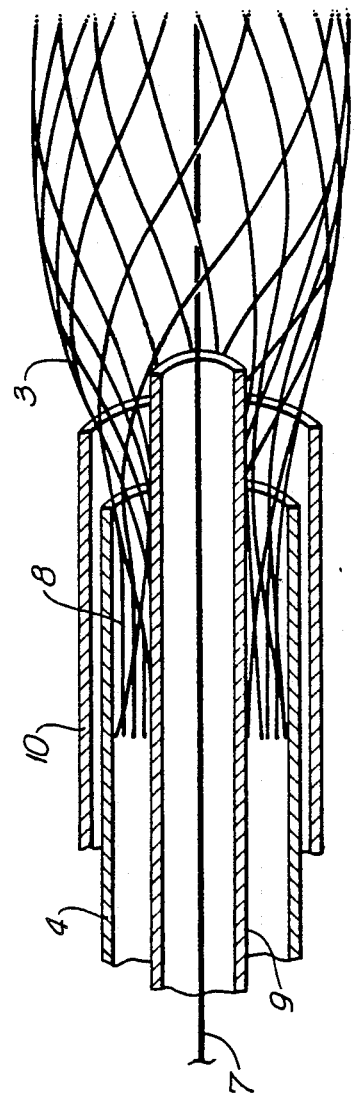
FIG. 3 is a longitudinal section of the fixation of the proximal end of the deformable cuff over the distal end of a catheter.

FIG. 3 is a larger-scale axial section of the proximal end of the deformable cuff 3. In this Figure we find again the flexible tube or catheter 4 and the axial wire 7.

Wires 8 which make up the end of the deformable cuff are unraveled, inserted and fixed parallel to the axis between the end of tube 4 and a second tube 9 which is placed inside the latter and in which wire 7 runs freely.

Tube 9 should preferibly extend over the entire length of tube 4. The ends of wire 8 are glued between tube 4 and tube 9.

It is recommended to slip a thermo-shinkeable sleeve 10 over the proximal end of the cuff and then heat-shrink it.

In FIG. 3 we see that the proximal end of the deformable cuff 3 which is fixed to catheter 4 and to the internal tube 9 slides freely over the pull wire 7.

FIG. 4 shows another embodiment of a device according to the invention.

When an inflatable balloon is introduced into an artery to correct a stenosis, the intervention generally begins with insertion into the artery of a guide wire of the piano-wire type. The catheter is then slipped over this wire bearing at its end the inflatable balloon through which passes a small axial tube which engages said wire and follows it.

When the stenosis has been eliminated, the balloon is deflated and withdrawn from the artery, but the guide wire may be left in place for some minutes in case it becomes necessary to use the balloon again.

The device according to FIG. 4 is designed to be used in this case.

The mark 11 represents a guide wire inserted into artery 1.

The device again includes a net 3 in form of a deformable cuff composed of interlocked wire mounted at the end of a small tube 4 and an axial wire 7 fixed to the distal end of the net which makes it possible to bring the latter closer to the proximal end in order to open the net or to push it farther away in order to close the latter. The distal end is loccated to the left in FIG. 4.

The device according to FIG. 4 also includes a small piece of tubing 12 which delimits an axial conduit 12a passing through the distal end of the cuff.

During application of the device according to FIG. 4, the end of the guide wire which extends outside the artery in conduit 12a is inserted and then turned back from the cuff towards the proximal end through the mesh of the net. This permits to guide the cuff until it reaches the zone where the stenosis had been located and previously corrected with an inflatable balloon.

During this insertion, the net 3 is in an elongated position. Once the device has arrived at the site, the axial wire 7 is pulled to open the net and bring it into the position shown in FIG. 4. It may be left in this position for several hours. Subsequently, the net is re-folded by pushing on the axial wire 7 and pulling on tube 4, and the catheter is withdrawn from the artery along guide wire 11.

FIGS. 5 and 6 represent another embodiment of a device according to the invention, including a netted cuff combined with an inflatable balloon.

To this date, inflatable balloons are used to correct the stenoses of the coronary arteries but only downstream from the common trunk, i.e. from the bifurcation of the circurnflex and interventricular anterior arteries. They are used only very exceptionally to intervene on the common trunk because of the fact that detachments of the wall in the common trunk occurring after the invervention with an inflatable balloon would deprive a large part of the heart of irrigation and thus cause almost instantaneous death.

FIGS. 5 and 6 show a device according to this invention which would permit interventions on stenoses of the common trunk and also on strictures located below the latter or on other arteries.

The devices according to FIG. 5 include a deformable balloon 13 of the kind currently used for angioplasty mounted at the end of a flexible tube 14. An axial tube 15 passes through the balloon from one end to the other and is fixed to the latter by one or both of its ends.

FIGS. 5 and 6 show an embodiment having two coaxial tubes 14 and 15.

As a variation, a single tube divided into two conduits by an inner partition could also be used.

Tubes 14 and 15 extend to the outside where they end in a funnel of a known type, for example a "LUER-LOCK" funnel, which may be simple or include a derivation for the injection of fluid into the catheter.

The axial tube 15 is to receive the guide wire 11 which has previously been introduced into the artery.

The interspace between tubes 14 and 15 is intended for injection or pumping of the inflation fluid into balloon 13.

The device also includes a net 3 in form of a cuff, composed of plaited wires surrounding the inflatable balloon, the distal end of which is fixed to the distal end of said balloon, while the proximal end slides freely on tube 14.

For the sake of clarity in the drawing, net 3 is shown partly cut away.

Net 3 is mounted at the end of a flexible tube 16 which encloses tubes 14 and 15.

The steps of practical application are the following:

When a stenosis is to be corrected, a guide wire 11 is first introduced into the artery. The axial tube 15 is then inserted over it and the device according to FIG. 5 is then pushed along guide wire 11 in a stretch, i.e. the balloon 13 is collapsed and net 3 is elongated. The progress is checked by radiography. Once the net and balloon are in place, a fluid is pumped in between tubes 14 and 15 which inflates the balloon and, in turn, dilates the artery and eliminates the stricture.

The highly flexible and deformable net 3 does not hamper the inflation of the balloon, since it slides in relation to the latter. The inflation of the balloon causes the dilation of the net.

Once the stricture has been eliminated, the fluid is withdrawn and the balloon is deflated, but the net remains in place against the internal wall of the artery. If necessary, the net is pressed against the wall of the artery by pushing on tube 16 which is sufficiently rigid to transmit the thrust. The axial tube 15 is held fast to immobilize the distal end.

The blood circulates through the mesh of the netting and the prothesis may be left in this position for a time on the order of one to several hours which is more than enough for the eventual detachments of the inner arterial wall to heal.

Subsequently, tube 16 is pulled while keeping the axial tube 15 in place which has the effect of moving the two ends of net 3 further apart and putting the latter back into an elongated position, then the entire complex of the device is pulled out of the artery along guide wire 11. In the embodiment according to FIGS. 5 and 6, it is not necessary to use a wire to cause the deformation of cuff 3. The central tube 15 which is fixed to the distal end of the net and tube 16 which is fixed to the proximal end of the net are sufficient to permit moving these two ends towards or away from each other.

What is claimed is:

1. A method of treating a patient's artery after the use of a catheter in an interventional procedure therein has damaged a section of arterial lining which can result in a blood flow restriction through the damaged arterial section, the method comprising:
    (a) withdrawing from the patient's artery the catheter used in the interventional procedure;
    (b) providing a separate catheter assembly having an elongated catheter body with an expandable member at the distal end thereof formed of interwoven strands of wire or fiber which are secured at the proximal and distal ends of the expandable member;
    (c) advancing the catheter assembly into and through the patient's arterial system until the expandable member is disposed within the damaged arterial section;
    (d) reducing the axial spacing between the distal and proximal ends of the expandable member to expand the expandable member to radially press the strands thereof against the damaged arterial lining and thereby expand the passageway through the damaged arterial section and increase the blood flow therethrough;
    (e) holding the expandable member stationary within the damaged arterial section in the expanded condition with the strands thereof pressing against the damaged arterial lining while blood flows through the arterial passageway for a period of sufficient length to ensure that the arterial lining within the damaged section is resecured to the arterial wall;
    (f) increasing the axial spacing between the proximal and distal ends of the expandable member at the end of said period to thereby reduce the radial dimension thereof so that the expandable member can be removed from the damaged arterial section; and
    (g) removing the catheter assembly from the patient's artery.

2. The method of claim 1 wherein a guidewire is first advanced through the patient's arterial system to a site therein for the interventional procedure and then after the interventional procedure the catheter assembly having the expandable member at the distal end thereof is advanced over the previously placed guidewire to the site having a flow restriction which results from the interventional procedure.

3. A method of treating a patient's artery after an interventional procedure therein has damaged the arterial lining resulting in a blood fow restriction in the passageway therethrough, the method comprising:
    (a) providing a catheter assembly having an expandable member at the distal end thereof formed of interwoven strands of wire or fiber which are secured at the proximal and distal ends of the expandable member;
    (b) advancing the catheter assembly through the patient's arterial system until the expandable member is disposed within the blood flow restriction in the arterial passageway;
    (c) reducing the axial spacing between the distal and proximal ends of the expandable member to increase the radial dimension thereof to radially press the strands thereof against the flow restriction and thereby expand the passageway and increase the blood flow therethrough;
    (d) holding the expandable member stationary in the expanded condition within the flow restriction while blood flows through the arterial passageway for an extended period of at least one hour;
    (e) increasing the axial spacing between the proximal and distal ends of the expandable member at the end of said period to thereby reduce the radial dimension thereof so that the expandable member can be removed from the site of the flow restriction; and
    (f) removing the catheter assembly from the patient's artery.

* * * * *